United States Patent [19]

Kaieda et al.

[11] Patent Number: 4,684,734

[45] Date of Patent: Aug. 4, 1987

[54] METHOD FOR MANUFACTURE OR ORGANIC FLUORINE COMPOUNDS

[75] Inventors: Osamu Kaieda, Osaka; Masaru Awashima, Suita; Isao Okitaka; Toshiaki Nakamura, both of Osaka, all of Japan

[73] Assignee: Nippon Shokubai KK Co., Ltd., Osaka, Japan

[21] Appl. No.: 776,085

[22] Filed: Sep. 13, 1985

Related U.S. Application Data

[63] Continuation of Ser. No. 580,849, Feb. 16, 1984, abandoned.

[30] Foreign Application Priority Data

| Feb. 18, 1983 | [JP] | Japan | 58-24848 |
| Oct. 31, 1983 | [JP] | Japan | 58-202590 |
| Nov. 24, 1983 | [JP] | Japan | 58-219473 |
| Nov. 24, 1983 | [JP] | Japan | 58-219474 |

[51] Int. Cl.$^4$ .................. C07C 120/00; C07C 121/50; C07D 213/61; C07D 213/00
[52] U.S. Cl. .................. 546/345; 546/286; 546/287; 546/289; 546/304; 546/307; 558/419; 558/423; 558/425; 568/933; 568/937; 568/938; 570/147
[58] Field of Search ............... 546/345, 286, 287, 289, 546/307, 304; 570/147; 260/465 G; 558/423, 425, 419; 568/933, 937, 938

[56] References Cited

U.S. PATENT DOCUMENTS

| 3,296,269 | 1/1967 | Boudakian | 546/345 |
| 3,303,197 | 2/1967 | Haszeldine et al. | 546/345 |
| 3,312,746 | 4/1967 | Fielding | 570/147 |
| 3,485,839 | 12/1969 | Fuller | 546/345 X |
| 3,574,775 | 4/1971 | Fuller | 570/147 |
| 4,174,349 | 11/1979 | Evans et al. | 570/147 X |
| 4,209,457 | 6/1980 | Fuller | 260/465 G |
| 4,229,365 | 10/1980 | Oeser et al. | 260/465 G |

FOREIGN PATENT DOCUMENTS

| 768204 | 12/1971 | Belgium | 546/345 |
| 0003344 | 8/1979 | European Pat. Off. | |
| 7120598 | 1/1972 | France | |
| 1256082 | 12/1971 | United Kingdom | 546/345 |
| 1272475 | 4/1972 | United Kingdom | 546/345 |
| 1340421 | 12/1973 | United Kingdom | |

OTHER PUBLICATIONS

Boudakian; J. Het. Chem., 5, (1968), pp. 683–684.
Tetrahedron Letters, 16, pp. 1429–1432, Pergamon Press, (1978) Bohme et al.

*Primary Examiner*—Joseph Paul Brust
*Attorney, Agent, or Firm*—Omri M. Behr

[57] ABSTRACT

Organic fluorine compounds such as pentafluorobenzonitrile, tetrafluorophthalonitriles, and pentafluoropyridine are produced by a method which comprises causing a chloro- or bromo-organic compound to react with a fluorinating agent such as an alkali metal fluoride in benzonitrile as a solvent at temperatures in the range of 190° to 400° C. under at least spontaneously generated pressure.

17 Claims, No Drawings

METHOD FOR MANUFACTURE OR ORGANIC FLUORINE COMPOUNDS

This application is a continuation of application Ser. No. 580,849, filed Feb. 16, 1984, now abandoned.

BACKGROUND OF THE INVENTION

1. Field of the Invention:

This invention relates to a method for the manufacture of organic fluorine compounds. More particularly, this invention relates to a method for the manufacture of organic fluorine compounds by the so-called halogen exchange reaction, i.e. the reaction of a chloro- or bromo-organic compound with a fluorinating agent in the medium of benzonitrile.

2. Description of Prior Arts:

The so-called halogen exchange reaction, namely the reaction of an alkali fluoride upon an aromatic halide for consequent substitution of the fluorine atom for the halogen atom has been known long to the art. Generally in this reaction, an aprotic polar solvent is used as the solvent for the reactants in use. Examples of the aprotic polar solvent are dimethyl sulfoxide (DMSO), sulfolane (TMSO$_2$), N-dimethylformamide (DMF), N-methyl-2-pyrrolidone (NMP) and dimethyl sulfone (DMSO$_2$). The halogen exchange reaction is carried out at a temperature not exceeding the boiling point of the solvent in use. [See, for example, Ishikawa: Journal of Synthetic Organic Chemistry, Japan, vol. 25, page 808 (1967) and M. Hudlicky: Chemistry of Organic Florine Compounds, page 112 (1976), John Wiley & Sons Press.] At times, the reaction system may incorporate therein a phase transfer catalyst such as a crown compound for the purpose of increasing the reaction velocity.

When the halogen exchange is carried out by the method described above, however, the halogens in those aromatic monohalides and aromatic polyhalides which have halogen substituents at the ortho or para positions of electron-attractive groups (such as, for example, —CN and —NO$_2$) easily undergo halogen exchange, while halogens at meta positions do not undergo halogen exchange at all. The aromatic halides on which halogen exchange can be effected by the aforementioned method generally are limited to aromatic halides having only small numbers of halogen substituents such as those represented by the synthesis of 2,6-difluorobenzo-nitrile from 2,6-dichlorobenzonitrile described in Ishikawa: Journal of Synthetic Organic Chemistry, Japan, Vol. 27, page 174 (1969). More often than not it is difficult to effect perfect halogen exchange on polyhalides of higher orders than those mentioned above. If perfect halogen exchange is obtained somehow or other on such polyhalides, the yields are poor.

The method described above does not suit the production of m-fluorobenzonitrile and 3,5-difluorobenzonitrile respectively from m-chlorobenzonitrile and 3,5-dichlorobenzonitrile which have halogen substituents at the meta positions of cyano groups. By the same token, this method does not suit the production of 3-fluoropyridine and 2,5-difluoropyridine respectively from 3-choloropyridine and 2,5-dichloropyridine which have halogen substituents at the meta positions of the nitrogen atoms having the electron attractive property. No process is reported in literature as having provided effective production of m-fluorobenzonitrile from m-chlorobenzonitrile, 3,5-difluorobenzonitrile from 3,5-dichlorobenzonitrile, 3-fluoropyridine from 3-chloropyridine, or 2,5-difluoropyridine from 2,5-dichloropyridine by halogen exchange reaction carried out in a solvent. Such is the true status of affairs.

A case of halogen exchange effected on 2,5-dichloropyridine is reported by G. G. Finger et al in J. Org. Chem., Vol. 23, page 1666 (1963). When 2,5-dichloropyridine is subjected to halogen exchange in DMSO$_2$ as a solvent by using potassium fluoride as a fluorinating agent, the reaction only produces 5-chloro-2-fluoropyridine and fails to afford 2,5-difluoropyridine.

Moreover, the method described above does not suit the production of pentafluorobenzonitrile and tetrafluoroisophthalonitrile respectively from pentachlorobenzonitrile and tetrachloroisophthalonitrile which are polyhalides and which have halogen substituents at the meta positons of cyano groups. It does not suit the production of pentafluoropyridine from pentachloropyridine which is a polyhalide and which has a halogen substituent at the meta position of the nitrogen atom having an electron attractive property. No process is reported in literature as having provided effective production of pentafluorobenzonitrile from pentachlorobenzonitrile, tetrafluoroisophthalonitrile from tetrachloroisophthalonitrile, or pentafluoropyridine from pentachloropyridine by halogen exchange effected in a solvent.

In fact, when pentachlorobenzonitrile is refluxed in dimethyl sulfoxide as a solvent in the presence of excess potassium fluoride for 24 hours in accordance with the method described above, the reaction produces 3,5-dichloro-2,4,6-trifluorobenzonitrile but fails to afford perfectly halogen exchanged pentafluorobenzonitrile at all. When the reaction is carried out under reflux in a solvent generally adopted in halogen exchange reaction, the results are the same as described above. The same results persist when the reaction system incorporates therein a phase transfer catalyst.

It has been ascertained by our research that for the halogen exchange reaction to be effected completely, the reaction temperature must be increased by the use of an autoclave. It has been further ascertained that when the reaction is carried out in any solvent generally adopted in the halogen exchange reaction except for benzonitrile which is specifically used for the present invention, the yield of the reaction is too low for the reaction to be economically feasible because, at elevated temperatures, the solvent undergoes decomposition or a secondary reaction with the reactants or with the product of the main reaction. M. Birchall et al report in J. Chem. Soc. (C) (1971), page 1341 a report on a method for synthesizing pentafluorobenzonitrile by treating pentachlorobenzonitrile at elevated temperatures of 300° to 480° C. with potassium fluoride as a fluorinating agent in an autoclave without use of a solvent. Their reaction performed at 350° C. for 20 hours is reported to have yielded about 70 mol % of pentafluorobenzonitrile based on pentachlorobenzonitrile. Since this reaction uses no solvent, it proceeds with generation of heat and this heat makes control of the reaction temperature difficult. At the end of the reaction, a large amount of carbonized materials remains fast to the vessel. All considered, this method proves to be hardly feasible from the economic point of view.

No method is reported in literature as having successfully synthesized tetrafluoroisophthalonitrile by halogen exchange from tetrachloroisophthalonitrile. Only a case of halogen exchange effected on tetrachloroisophthalonitrile is reported by Ishikawa et al in Journal of Industrial Chemistry, Vol. 73, page 447 (1970). When the halogen exchange reaction is carried out in DMF as a solvent with potassium fluoride as a fluorinating agent, it barely produces 5-chloro-2,4,6-trifluoroisophthalonitrile and fails to afford perfectly substituted tetrafluoroisophthalonitrile.

Methods for producing tetrafluoroterephthalonitrile by halogen exchange of tetrachloroterephthalonitrile, a polyhalide, by using solvents of ordinary run have been suggested in French Pat. No. 1,397,521 (1965) and Japanese patent Open (Kokai) SHO No. 51(1976)-6940. Neither of these methods produce tetrafluoroterephthalonitrile in satisfactory yields. The ordinary solvents used in these methods are such that when the reaction temperature is elevated or the reaction is protracted for the purpose of improving yields, these solvents undergo decomposition or undergo secondary reaction with the reactants or with the products of main reaction only to impair yields. These methods have another disadvantage that even if the used solvents are recovered, the hardly suit commercial use. The method which effects the reaction at high temperature of 200° to 400° C. in an autoclave without use of a solvent finds general recognition as one approach to avoiding the drawback that such solvents are not usable at elevated temperatures. A case of halogen exchange effected on tetrachloroterephtalonitrile at 300° C. in an autoclave without use of a solvent to produce tetrafluoroterephthalonitrile is reported, for example, by Ueda et al in Bull. Chem. Soc. Japan, Vol. 40, page 688. Since this reaction uses no solvent, it proceeds with generation of heat and the heat thus generated renders the control of the reaction temperature difficult. At the end of the reaction, a large amount of carbonized materials remains fast to the vessel. Thus, this method proves to be hardly feasible from the economic point of view.

R. E. Banks et al report in J. Chem. Soc., page 594 (1965) a halogen exchange reaction accomplished on pentachloropyridine in NMP as a solvent at the boiling point of this solvent. This reaction preponderantly produces 3,5-dichloro-2,4,6-trifluoropyridine and fails to produce perfectly halogen exchanged pentafluoropyridine. The solvent generally adopted for this reaction is such that when the reaction temperature is increased or the reaction time is protracted for the purpose of improving the yield of the reaction, the solvent undergoes decomposition or undergoes secondary reaction with the reactants or with the product of the main reaction only to impair the yield. This method has another disadvantage that the used solvent, even if recovered, does not suit commercial use. The solvents usable in this method have a disadvantage that they cannot be effectively used at elevated temperatures. The method which effects the reaction at elevated temperatures of 200° to 500° C. in an autoclave in the absence of a solvent finds general recognition as one approach to avoiding the drawback that such solvents are not usable at high temperatures. A case of halogen exchange effected on pentachloropyridine at 500° C. in an autoclave in the absence of a solvent to produce pentafluoropyridine is reported by R. E. Banks et al. in J. Chem. Soc., page 594 (1965). Because this reaction uses no solvent, it proceeds with generation of heat and this heat renders the control of the reaction temperature difficult. Moreover, a large amount of carbonized materials remains fast to the vessel. Thus, this method proves to be hardly feasible from the economic point of view.

OBJECT OF THE INVENTION

An object of this invention, therefore, resides in providing a novel method for the manufacture of organic fluorine compounds.

Another object of this invention is to provide a method for the manufacture of organic fluorine compounds by the reaction of a chloro- or bromo-organic compound with a fluorinating agent in benzonitrile as a medium.

Yet another object of this invention is to provide a method for the manufacture of a fluorinated aromatic compound in a high yield by the halogen exchange reaction of a chloro- or bromo-aromatic compound with a fluorinating agent.

SUMMARY OF THE INVENTION

The object described above are accomplished by this invention providing a method for the manufacture of organic fluorine compounds, which method comprises causing a chloro- or bromo-organic compound to react with a fluorinating agent in benzonitrile as a solvent at temperatures in the range of 190° to 400° C. under at least the pressure spontaneously generated in consequence of the reaction.

PREFERRED EMBODIMENT OF THE INVENTION

The benzonitrile to be used as a solvent in this invention is thermally stable. In the halogen exchange of a chloro- or bromo-organic compound for conversion into a corresponding organic fluorine compounds, this solvent remains intact at elevated temperatures used for the reaction. This solvent, unlike other solvents, does not undergo secondary reaction with the reactants or with the product of the main reaction. Thus, it can be used effectively at elevated temperature in the range of 190° to 400° C. The reaction, therefore, can be carried out at an increased reaction velocity and the yield similarly improved. This solvent has an advantage that it is free from the secondary reaction which some other solvent would undergo with the reactants or with the product of the main reaction. Unlike the method which finds no use for any solvent, the method of this invention, owing to the use of this solvent, permits the reaction temperature to be easily controlled and precludes otherwise possible occurrence of a large amount of carbonized materials. When this method is worked commercially, therefore, it enables the product aimed at to be obtained in a high yield.

Unlike aprotic polar solvents which are used generally, the benzonitrile used as the solvent in this invention has only a minimal ability to dissolve inorganic salts at temperatures below its boiling point. In the ordinary halogen exchange reaction now in common use, there must be used a solvent capable of dissolving a fluoride being used as a fluorinating agent. Thus, the conventional halogen exchange reaction uses an aprotic polar solvent such as, for example, DMSO, $TMSO_2$, DMF, MNP or $DMSO_2$ which is highly capable of dissolving inorganic salts. Use of benzonitrile, a solvent which is minimally capable of dissolving inorganic salts, as contemplated in this invention has been set aside as disadvantageous for the conventional halogen exchange. For example, G. C. Finger et al. report in J. Amer. Chem. So., Vol. 78, page 6034 (1956) a case of halogen exchange effected on 2,4-dinitrochlorobenzene in benzonitrile as a solvent with potassium fluoride as a fluorinating agent to produce 2,4-dinitrofluorobenzene. This reaction, however, affords the product in a low yield because the reaction temperature is low, in the range of 150° to 170° C. As reported in J. Chem. Soc., page 6264 (1965), G. Fuller has tested solvents for use in the halogen exchange of hexachlorobenzene with potassium fluoride as a fluorinating agent. In the test, he has failed to effect the halogen exchange by performing the reaction in benzonitrile, among other solvents, at 175° C. for 18 hours.

By our study, it has been ascertained that when benzonitrile is used at temperatures exceeding the boiling point thereof, the solubility of the fluorinating agent such as potassium fluoride is sharply increased and that in the case of the present invention, the reaction proceeds advantageously when it is performed at temperatures in the range of 190° to 400° C., preferably 230° to 360° C. The strikingly high yield in which this invention affords the organic fluorine compound may be safely ascribed to the fact that the use of benzonitrile as the solvent brings about advantageous temperature effects and, at the same time, increases the solubility of the fluorinating agent.

Generally, halogen exchange is difficult to effect on polyhalides. On such polyhalides, the halogen exchange is attained in low yields as reported in R. E. Banks et al: Chem. & Ind., Vol. 1964, page 835 and Ishikawa: Nippon Kagaku Kaishi, Vol. 86, page 962 (1965). In the present invention, the halogen exchange can be easily effected in high yields. It has been held that halogens at the meta positions in the electron attractive groups such as —CN group and —$NO_2$ group in the aromatic compounds are not easily substituted. This invention permits substitution of such halogens at the meta positions.

As the starting material for the reaction contemplated by this inveniton, any chloro- or bromo-organic compound can be used so far as the compound has at least one chlorine atom or bromine atom. Further, a chloro- or bromo-organic compound in which fluorine has already substituted for part of the chlorine or bromine atoms can be as effectively used. Among other chloro- and bromo-aromatic compounds described above, chloro- and bromo-organic compounds and particularly the chloro- and bromo-aromatic compounds represented by the following general formula I prove advantageous for the present invention.

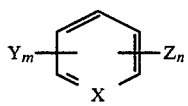
(I)

wherein X denotes N, —CY or —CZ where Y is Cl or Br and Z is F, CN or $NO_2$, m denotes an integer of the value of 1 to 5, and n an integer of the value of 0 to 4, providing that the sum of m and n is an integer of the value not more than 5.

Among the compounds represented by the general formula I, those represented by the general formula II or III are advantageous.

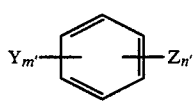
(II)

wherein Y denotes Cl or Br, Z denotes F, CN or $NO_2$, m' denotes an integer of the value of 1 to 6, and n' denotes an integer of the value of 0 to 5, providing that the sum of m' and n' is an integer of the value of not more than 6.

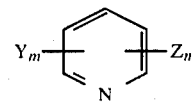
(III)

wherein Y denotes Cl or Br, Z denotes F, CN or $NO_2$, m denotes an integer of the value of 1 to 5, and n denotes an integer of the value of 0 to 4, providing that the sum of m and n is an integer of the value of not more than 5.

Further, among the compounds represented by the general formula II, those compounds represented by the general formula IV or V are advantageous.

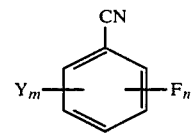
(IV)

wherein m denotes an integer of the value of 1 to 5 and n denotes an integer of the value of 0 to 4, providing that the sum of m and n is an integer of the value of not more than 5.

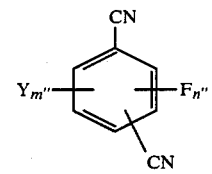
(V)

wherein Y denotes Cl or Br, m" denotes an integer of the value of 1 to 4, and n" denotes an integer of the value of 0 to 3, providing that the sum of m" and n" is an integer of the value of not more than 4.

Moreover, among the compoundsd represented by the general formula III, those compounds represented by the general formula VI and VII are advantageous.

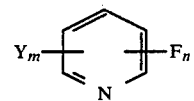
(VI)

wherein Y denotes Cl or Br, m denotes an integer of the value of 1 to 5, and n denotes an integer of the value of 0 to 4, providing that the sum of m and n is an integer of the value of not more than 5.

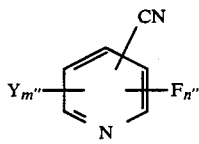
(VII)

wherein Y denotes Cl or Br, m" denotes an integer of the value of 1 to 4, and n" denotes an integer of the value of 0 to 3, providing that the sum of m" and n" is an integer of the value of not more than 4.

Typical examples include chlorobenzene, polychlorobenzenes, o-chloronitrobenzene, m-chloronitrobenzene, p-chloronitrobenzene, 2,4-dinitrochlorobenzene, o-chlorobenzonitrile, m-chlobenzonitrile, p-chlorobenzonitrile, 2,6-dichlorobenzonitrile, 3,5-dichlorobenzonitrile, 3,5-dichloro-2,4,6-trifluorbenzonitrile, 3-chloro-2,4,5,6-tetrafluorobenzonitrile, pentachlorobenzonitrile, 3-chlorophthalonitrile, 3,6-dichlorophthalonitrile, 4,5-dichlorophthalonitrile, tetrachlorophthalonitrile, 5-chloroisophthalonitrile, 5-chloro-2,4,6-trifluoroisophthalonitrile, tetrachloroisophthalonitrile, 2,3-dichloroterephthalonitrile, tetrachloroterephthalonitrile, 3-chloropyridine, 2,5-dichloropyridine, 2,3,5-trichloropyridine, 3,5-dichloro-2,4,6-trifluoropyridine, pentachloropyridine, -5-chloropyridine-3-nitrile, 6-chloropyridine-3-nitrile, 5-chloro-2,4,6-trifluoropyridine-3-nitrile, 2,4,5,6-tetrachloropyridine-3-nitrile, 6-chloropyridine-2-nitrile, 2,3,5,6-tetrachloropyridine-4-nitrile and 3,4,5,6-tetrachloropyridine-2-nitrile, etc., and the compounds obtained by having bromine atom substituted for the chlorine atoms in the compounds enumerated above.

Examples of the fluorinating agent to be advantageously used generally in the halogen exchange reaction include alkali metal fluorides such as cesium fluoride, potassium fluoride, sodium fluoride and lithium fluoride and alkaline earth metal fluorides such as calcium fluoride, barium fluoride and magnesium fluoride. At times, fluorides of transient metals such as antimony fluoride may be used. In the present invention, any of the fluorinating agents which have found popular acceptance can be used advantageously. Among other fluorinating agents, alkali metal fluorides or alkaline earth metal fluorides which are easy to handle and which are readily available commercially prove particularly desirable. Especially alkali metal fluorides are preferred over alkaline earth metal fluorides. In all the fluorinating agents usable at all, potassium fluoride is the best choice.

The fluorinating agent is required to be used in an amount at least equivalent to the chlorine or bromine atom to be substituted by the fluorine atom in the chloro- or bromo-organic compound being used as the starting material. In the case of an alkali metal fluoride, the amount of the fluorinating agent advantageously used is in the range of 1 to 2 moles based on the chlorine or bromine atom.

In this invention, the reaction is desired to proceed under the pressure which is spontaneously generated in consequence of the reaction. Optionally the pressure of the reaction system may be increased by the used of an inert gas such as air. Generally the reaction is carried out at temperatures in the range of 190° to 400° C. under pressure of 0 to about 30 kg/cm$^2$ (gauge), preferably at temperatures in the range of 230° to 360° C. under pressure of about 1.5 to about 22 kg/cm$^2$ (gauge).

The reaction temperature is defined to be in the range of 190° to 400° C., preferably in the range of 230° to 360° C. as described above. The optimum reaction temperature is variable with the kind of the starting material to be used. When a compound of the general formula IV is used as a starting material, for example, the reaction temperature is in the range of 270° to 400° C. (4 to 30 kg/cm$^2$·G), preferably in the range of 300° to 350° C. (7 to 20 kg/cm$^2$·G). When a compound of the general formula V is used as a starting material, the reaction temperature is in the range of 190° to 400° C. (0 to 28 kg/cm$^2$·G). Particularly in the case of tetrachlorophthalonitrile, the reaction temperature is in the range of 190° to 300° C. (0 to 11 kg/cm$^2$·G). In the case of tetrachloroisophthalonitrile, the reaction temperature is in the range of 250° to 350° C. (2.5 to 18 kg/cm$^2$·G). In the case of tetrachloroterephthalonitrile, the reaction temperature is in the range of 210° to 330° C. (0.7 to 15 kg/cm$^2$·G). When a compound of the general formula VI is used as a starting material, the reaction temperature is in the range of 300° to 400° C. (7 to 30 kg/cm$^2$·G), preferably in the range of 330° to 380° C. (10 to 26 kg/cm$^2$·G). When a compound of the general formula VII is used as a starting material reaction temperature is in the range of 190° to 400° C. (0 to 30 kg/cm$^2$·G), preferably in the range of 210° to 350° C. (0.7 to 20 kg/cm$^2$·G).

The reaction time which is suitable for this reaction is in the range of about 2 to about 48 hours, although it is variable with the reaction temperature and the kind of the starting material.

As the raw material, the chloro- or bromo-organic compound is added to the reaction system in an amount of about 5 to about 50 parts by weight, preferably 20 to 40 parts by weight, based on 100 parts by weight of benzonitrile as the solvent.

In the reaction of the present invention, when the reaction temperature is low and the reaction time is short, there may be partly formed a reaction product in which the chlorine or bromine has not been completely subsutituted. Where the compound aimed at by the reaction has a lower boiling point such as the boiling point of pentafluorobenzonitrile (161° C. under 760 mmHg) or that of pentafluoropyridine (84° C. under 760 mmHg) than the boiling point of benzonitrile (191° C. under 760 mmHg) which is the solvent, the compound produced can be separated by stripping. In the kettle, a chlorine- or bromine-containing fluorine compound of a high boiling point remains dissolved in the benzonitrile solvent. The benzonitrile solution thus remaining in the kettle may be recovered and put to use again in the reaction. In the next reaction, the chlorine- or bromine-containing fluorine compound contained therein as an unaltered intermediate is readily converted into the compound aimed at by the main reaction. The reuse of the recovered benzonitrile solution contributes to increasing the yield of the product of the reaction such as pentafluorobenzonitrile or pentafluoropyridine.

Generally, it is held that the halogen exchange reaction is carried out advantageously in the absence of water because the reaction velocity can be increased and the occurrence of secondary reaction curbed under the anhydrous condition. Aprotic polar solvents such as DMSO, TMSO$_2$, DMF, NMP and DMSO$_2$ which find popular acceptance have high hygroscopicity and contain fairly large volumes of water. Thus, such an aprotic polar solvent must be combined with benzene or toluene and distilled to expel the water in the form of azeotrope in advance of the reaction. In contrast, the benzonitrile which is used in the present invention lacks hygroscopicity and, therefore, finds no use for such troublesome treatment. Potassium fluoride which is used as the fluorinating agent has high hygroscopicity and may at times be required to be combined with benzene or toluene and distilled to expel the water in the form of azeotrope in advance of the reaction.

For the reaction of the present invention, additional incorporation of a phase transfer catalyst in the reaction system proves advantageous. When the reaction system contain the phase transfer catalyst, there is derived an advantage that the reaction velocity can be increased and the reaction time shortened. As the phase transfer catalyst, a crown compound such as dibenzo-18-crown-6-ether or polyethylene glycol having a molecular weight of 300 to 600 can be used. The amount of the phase transfer catalyst to be advantageously used in the reaction system is in the range of 0.01 to 0.25 mol, preferably 0.05 to 0.20 mol, per mol of the chloro- or bromo-organic compound as the raw material.

As the product of the reaction of this invention, there is obtained an organic fluorine compound which corresponds to the compound used as the starting material for the reaction. Among other organic fluorine compounds thus produced, fluorinated aromatic compounds prove to be advantageous. In such fluorinated aromatic compounds, those fluorinated aromatic compounds represented by the following general formula VIII are particularly desirable.

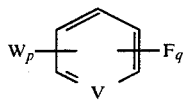
(VIII)

wherein V denotes N, —CW or —CF where W is Cl, Br, CN or NO$_2$, p denotes an integer of the value of 0 to 4, and q denotes an integer of the value of 1 to 5, providing that the sum of p and q is an integer of the value of not more than 5.

In the comopunds represented by the general formula VIII, the compounds represented by the following general formula IX or X prove particularly desirable.

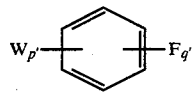
(IX)

wherein W is as defined above, p' denotes an integer of the value of 0 to 5, and q' denotes an integer of the value of 1 to 6, providing that the sum of p and q is an integer of the value of not more than 6.

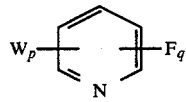
(X)

wherein W, p, and q are as defined above.

Further in the compounds represented by the general formula IX, the comopunds represented by the following general formula XI or XII prove particularly desirable.

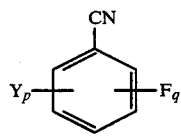
(XI)

wherein Y denotes Cl or Br, p denotes an integer of the value of 0 to 4, and q denotes an integer of the value of 1 to 5, providing that the sum of p and q is an integer of the value of not more than 5.

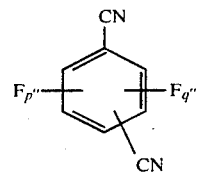
(XII)

wherein Y denotes Cl or Br, p" denotes an integer of the value of 0 to 3, and q" denotes an integer of the value of 1 to 4, providing that the sum of p" and q" is an integer of the value of not more than 4.

Further in the compounds of the general formula X, the compounds represented by the following general formula XIII or XIV prove particularly desirable.

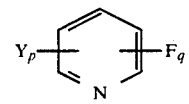
(XIII)

wherein Y, p and q are as defined above.

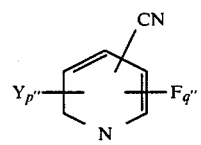
(XIV)

wherein Y, p" and q" are as defined above.

Typical examples include fluorobenzene, polyfluorobenzenes, o-fluoronitrobenzene, m-fluoronitrobenzene, p-fluoronitrobenzene, 2,4-dinitrofluorobenzene, o-fluorobenzonitrile, m-fluorobenzonitrile, p-fluorobenzonitrile, 2,6-difluorobenzonitrile, 3,5-difluorobenzonitrile, 3,5-difluoro-2,4,6-trichlorobenzonitrile, pentafluorobenzonitrile, 3-fluorophthalonitrile, 3,6-difluorophthalonitrile, 4,5-difluorophthalonitrile, tetrafluorophthalonitrile, 5-fluoroisophthalonitrile, 5-chloro-2,4,6-trifluoroisophthalonitrile, tetrafluoroisophthalonitrile, 2,3-difluoroterephthalonitrile, tetrafluoroterephthalonitrile, 3-fluoropyridine, 2,5-difluoropyridine, 2,3,5-trifluoropyridine, 3,5-dichlro-2,4,6-trifluoropyridine, pentafluoropyridine, 5-fluoropyridine-3-nitrile, 6-fluoropyridine-3-nitrile, 5-chloro-2,4,6-trifluoropyridine-3-nitrile, 6-fluoropyridine-4-nitrile, 2,3,5,6-tetrafluoropyridine-4-nitrile 3,4,5,6-tetrafluoropyridine-2-nitrile, etc., which are useful compounds as intermediates for the synthesis of agricultural pesticides, medicines and dyestuffs.

In the reaction of the present invention, benzonitrile as the solvent can be easily isolated by distillation from the reaction product and can be put to use as the solvent in the subsequent reaction.

Now, present invention will be described more specifically below with reference to working examples. It should be noted that the present invention is not limited to these examples.

EXAMPLE 1

An autoclave made of stainless steel and having an inner volume of 500 cc was charged with 200 g of benzonitrile, 60.0 g (0.218 mol) of pentachlorobenzonitrile and 69.7 g (1.20 mols) of finely divided dry potassium fluoride. After the air in the vessel was displaced with nitrogen gas, the contents of the vessel were stirred at 315° C. (under 12.5 kg/cm$^2$·G) for 18 hours. After the reaction terminated, the reaction mixture was cooled to room temperature and the potassium chloride and the unaltered potassium fluoride suspended therein were removed by filtration. When the benzonitrile solution remaining as the mother liquid in the vessel was analyzed by the internal standard method with a gas chromatography using 2 m of a packing agent (Apiezone Grease M) at a column temperature of 150° C., it was found to contain 80.5 mol % of pentafluorobenzonitrile and 1.2 mol % of 3,5-dichloro-2,4,6-trifluorobenzonitrile based on the amount of pentachlorobenzonitrile first placed in the autoclave. When the mother liquid was analyzed by gas chromatography using 2 m of a packing agent (Thermon 1000) at a column temperature of 90° C., it was found to contain 4.3 mol % of 3-chloro-2,4,5,6-tetrafluorobenzonitrile based on the amount of pentachlorobenzonitrile first placed in the autoclave. One half of the mother liquid was accurately weighed out and treated with a precision fractional distillation unit, to obtain 15.9 g (75.5 mol % in yield) of pentafluorobenzonitrile (as a fraction at 160° to 163° C. under normal pressure) as the product aimed at by the reaction. When this fraction was analyzed by gas chromatography, virtually no discernible peak of any substance other than pentafluorobenzonitrile was detected.

EXAMPLE 2

An autoclave having an inner volume of 500 cc was charged with the same raw materials as used in Example 1, except that 11.5 g (0,0319 mol) of dibenzo-18-crown-6-ether was dissolved in benzonitrile. The contents of the vessel were stirred at 300° C. (under 10.0 kg/cm$^2$·G) for seven hours. After the reaction was terminated, the reaction mixture was treated by following the procedure of Example 1. When the mother liquid consequently obtained was analyzed by gas chromatography, it was found to contain 66.5 mol % of pentafluorobenzonitrile, 15.4 mol % of 3-chloro-2,4,5,6-tetrafluorobenzonitrile and 5.8 mol % of 3,5-dichloro-2,4,6-trifluorobenzonitrile based on the amount of pentachlorobenzonitrile first placed in the vessel.

EXAMPLE 3

An autoclave having an inner volume of 500 cc was charged with the same raw materials as used in Example 1. The contents of the vessel were stirred at 350° C. (under 17.0 kg/cm$^2$·G) for four hours. After the reaction was terminated, the reaction mixture was treated by following the procedure of Example 1. When the mother liquid consequently obtained was analyzed by gas chromatography, it was found to contain 72.5 mol % of pentafluorobenzonitrile based on the amount of pentachlorobenzonitrile first places in the vessel.

EXAMPLE 4

An autoclave made of stainless steel and having an inner volume of 100 cc was charged with 40 g of benzonitrile, 16 g (0.0322 mol) of pentabromobenzonitrile and 10.3 g (0.177 mol) of finely divided dry potassium fluoride. After the air in the reaction vessel was displaced with nitrogen gas, the contents of vessel were stirred at 300° C. (under 9.5 kg/cm$^2$·G) for 20 hours. After the reaction was terminated, the reaction mixture was treated by following the procedure of Example 1. When the mother liquid consequently obtained was analyzed by gas chromatography, it was found to contain 71.9 mol % of pentafluorobenzonitrile based on the amount of pentabromobenzonitrile first placed in the reaction vessel.

EXAMPLE 5

An autoclave made of stainless steel and having an inner volume of 500 cc was charged with 200 g of benzonitrile, 80.0 g (0.291 mol) of pentachlorobenzonitrile and 65.9 g (1.135 mol) of finely divided dry potassium fluoride. After the air in the reaction vessel was displaced with nitrogen gas, the contents of the vessel were stirred at 270° C. (under 7.0 kg/cm$^2$·G) for four hours. After the reaction was terminated, the reaction solution was separated from potassium chloride and unaltered potassium fluoride by the use of a rotary evaporator under the final conditions of 180° C. of external temperature and 20 Torrs of vacuum. By treating the reaction solution with a precision fractional distillation device, there was recovered 56.8 g of 3,5-dichloro-2,4,6-trifluorobenzonitrile (a fraction at 222° to 224° C. under normal pressure) (86.3% in yield based on the amount of pentachlorobenzonitrile first placed in the reaction vessel, 98.2% in purity).

EXAMPLE 6

An autoclave made of stainless steel and having an inner volume of 500 cc was charged with 200 g of benzonitrile, 80.0 g (0.354 mol) of 3,5-dichloro-2,4,6-trifluorobenzonitrile and 45.2 g (0.779 mol) of finely divided dry potassium fluoride. After the air in the reaction vessel was displaced with nitrogen gas, the contents of the vessel were stirred at 330° C. (under 14.0 kg/cm$^2$·G) for 12 hours. After the reaction was terminated, the reaction solution was separated from potassium chloride and unaltered potassium fluoride with a rotary evaporator at 150° to 180° C. under a vacuum. When the separated solution was analyzed by gas chromatography using 2 m of a packing agent (Thermon 1000) at a column temperature of 60° C., it was found to contain 96.8 mol % of pentafluorobenzonitrile based on the amount of 3,5-dichloro-2,4,6-trifluorogenzonitrile first placed in the vessel.

By treating the separted solution with a precision fractional distillation device, there was recovered 62.8 g of pentafluorobenzonitrile as the product aimed at by the reaction. When this fraction was analyzed by gas chromatography, virtually no discernible peak of any substance other than pentafluorobenzonitrile was detected.

EXAMPLE 7

An autoclave made of stainless steel and having an inner volume of 500 cc was charged with 200 g of benzonitrile, 80.0 g (0.301 mol) of tetrachloroisophthalonitrile and 83.9 g (1.445 mol) of finely divided, dry potassium fluoride. After the air in the reaction vessel displaced with nitrogen gas, the contents of the reaction vessel were stirred at 320° C. (under 13.0 kg/cm$^2$·G) for 18 hours. After the reaction was terminated, the reaction mixture thus produced was cooled to room temperature and potassium chloride and unaltered potassium fluoride suspended therein were removed from the reaction mixture by filtration. The benzonitrile solution which remained as the mother liquid was analyzed by the inner standard method using a gas chromatography using 1 m of a packing agent (SE 52) at a column temperature of 60° C. Consequently, there was obtained 90.5 mol % of tetrafluoroisophthalonitrile based on the amount of tetrachloroisophthalonitrile first placed in the reaction vessel. In the chart of the analyses, virtually no discernible peak of any other substance such as unsubstituted isophthalonitrile was detected. By the gas chromatographic mass spectrometry (70 eV/ m/e=200, 131, 100, 31), the peak was confirmed to be that of tetrafluoroisophthalonitrile. By expelling the solvent benzonitrile from the aforementioned mother liquid through vacuum distillation, there was recovered 52.5 g of tetrafluoroisophthalonitrile in the form of crystals (M.P.; 73° to 76° C.). By elementray analysis, the crystals were found to consist of 48.0% of carbon, 38.3% of fluorine, and 13.7% of nitrogen (theoretically 48% of carbon, 38% of fluorine and 14% of nitrogen).

EXAMPLE 8

An autoclave having an inner volume of 500 cc was charged with the same raw materials as used in Example 7, except that 5.8 g (0.016 mol) of dibenzo-18-crown-6-ether was dissolved in benzonitrile. The contents of the vessel was stirred at 280° C. (under 7.0 kg/cm$^2$·G) for 10 hours. After the reaction terminated, the resultant reaction mixture was treated by following the procedure of Example 7. When the mother liquid consequently obtained was analyzed by gas chromatography, it was found to contain 70.2 mol % of tetrafluoroisophthalonitrile and 18.7 mol % of 5-chloro-2,4,6-trifluoroisophthalonitrile based on the amount of tetrachloroisophthalonitrile first placed in the vessel.

EXAMPLE 9

An autoclave having an inner volume of 500 cc was charged with the same raw materials as used in Example 7, except that tetrachloroterephthalonitrile was used as the starting material in the place of tetrachloroisophthalonitrile. The contents of the vessel were stirred at 270° C. (under 6.0 kg/cm$^2$·G) for 12 hours. After the reaction terminated, the resultant reaction mixture was treated by following the procedure of Example 7. When the mother liquid consequently obtained was analyzed by gas chromatography, it was found to contain 92.2 mol % of tetrafluoroerephthalonitrile based on the amount of tetrachloroterephthalonitrile first placed in the vessel. By expelling the solvent benzonitrile from this mother liquid through vacuum distillation, there was obtained tetrafluoroterephthalonitrile in the form of crystals (M.P.; 195°-197° C.).

EXAMPLE 10

An autoclave made of stainless steel and having an inner volume of 500 cc was charged with 200 g of benzonitrile, 80.0 g (0.301 mol) of tetrachloroorthophthalonitrile, and 83.9 g (1.444 mols) of finely divided dry potassium fluoride. After the air in the reaction vessel was displaced with nitrogen gas, the contents of the vessel were stirred at 230° C. (under 2.0 kg/cm$^2$·G) for 10 hours. After the reaction terminated, the resultant reaction mixture was cooled to room temperature and potassium chloride and unaltered potassium fluoride suspended in the reaction mixture were removed by filtration. When the benzonitrile solution remaining as the mother liquid was analyzed by gas chromatography using 1 ml of a packing agent (SE 52) at a column temperature of 60° C., it was found to contain 87.7 mol % of tetrafluoroorthophthalonitrile based on the amount of tetrachloroorthophthalonitrile first placed in the vessel.

By expelling benzonitrile from the mother liquid through vacuum distillation, there were obtained crystals of tetrafluoroorthophthalonitrile (M.P.; 86°-87° C.) which solidified at room temperature.

EXAMPLE 11

An autoclave made of stainless steel and having an inner volume of 500 cc was charged with 200 g of benzonitrile, 50.0 g (0.200 mol) of pentachloropyridine, and 69.7 g (1.20 mols) of finely divided dry potassium fluoride. After the air in the reaction vessel was displaced with nitrogen gas, the contents of the vessel were stirred at 365° C. (under 20.5 kg/cm$^2$·G) for 30 hours. After the reaction terminated, the reaction solution was freed from potassium chloride and unaltered potassium fluoride with a rotary evaporator under the final conditions of 160° C. of external temperature and 20 Torrs of vacuum. When the separated solution was analyzed by gas chromatography using 2 m of a packing agent (Thermon 1000) at a column temperature of 60° C., it was found to contain 54.2 mol % of pentafluoropyridiine, 9.3 mol % of 3-chloro-2,4,5,6,-tetrafluoropyridine and 26.6 mol % of 3,5-dichloro-2,4,6-trifluoropyridine respectively based on the amount of pentachloropyridine first placed in the vessel.

By treating the separated solution with a precision fractional distillation device, there was obtained 17.9 g of pentafluoropyridine (fraction at 83° to 85° C. under normal pressure) as the product aimed at. When this fraction was analyzed by gas chromatography, virtually no discernible peak of any substance other than pentafluoropyridine was detected.

EXAMPLE 12

An autoclave having an inner volume of 500 cc was charged with the same raw materials as used in Example 11, except that 11.5 g (0.0319 mol) of dibenzo-18-crown-6-ether was dissolved in benzonitrile. The contents of the vessel was stirred at 330° C. (under 15.0 kg/cm$^2$·G) for 24 hours. After the reaction terminated, the resultant reaction mixture was treated by following the procedure of Example 11. When the mother liquid consequently obtained was analyzed by gas chromatography, it was found to contain 25.7 mol % of pentafluoropyridine, 13.2 mol % of 3-chloro-2,4,5,6-tetrafluoropyridine and 54.3 mol % of 3,5-dichloro-2,4,6-trifluoropyridine respectively based on the amount of pentachloropyridine first palced in the vessel.

EXAMPLE 13

An autoclave made of stainless steel and having an inner volume of 200 cc was charged with 100 g of benzonitrile, 40 g (0.165 mol) of 2,4,5,6-tetrachloropyridine-3-nitrile and 46 g (0.790 mol) of finely divided dry potassium fluoride. After the air in the vessel was displaced with nitrogen gas, the contents of the vessel were stirred at 320° C. (under 13.5 kg/cm$^2$·G) for 10 hours. After the reaction terminated, the resultant reaction solution was freed from potassium chloride and unaltered potassium fluoride by the use of a rotary evaporator under the final conditions of 160° C. of outer temperature and 20 Torrs of vacuum. When the separated solution was analyzed by gas chromatography using 1 m of a packing agent (SE 52) at a column temperature of 60° C., it was found to contain 79.4 mol % of 2,4,5,6-tetrafluoropyridine-3-nitrile and 5.1 mol % of 5-chloro-2,4,6-trifluoropyridine-3-nitrile respectively based on the amount of 2,4,5,6-tetrachloropyridine-3-nitrile first placed in the vessel.

When the separated solution was treated with a precision fractional distillation device, there was recovered 22 g of 2,4,5,6-tetrafluoropyridine-3-nitrile (fraction at 165°–166° C. under normal pressure) as the product aimed at. When this fraction was analyzed by gas chromatography, virtually no discernible peak of any substance other than 2,4,5,6-tetrafluoropyridine-3-nitrile was detected.

EXAMPLE 14

An autoclave made of stainless steel and having an inner volume of 100 cc was charged with 40 g of benzonitrile, 8 g (0.0632 mol) of orthochloro-toluene and 7.33 g (0.1265 mol) of finely divided dry potassium fluoride. After the air in the vessel was displaced with nitrogen gas, the contents of the vessel were stirred at 370° C. (under 21.5 kg/cm$^2$·G) for 24 hours. By the use of a rotary evaporator, the reaction solution was freed from potassium chloride and unaltered potassium fluoride under a vacuum. When the separated benzonitrile solution was analyzed by gas chromatography using 2 m of a packing agent (Thermon 1000) at a column temperature of 60° C., it was found to contain 22 mol % of orthofluoro-toluene based on the amount of orthochloro-toluene first placed in the vessel.

EXAMPLE 15

An autoclave made of stainless steel and having an inner volume of 100 cc was charged with 40 g of benzonitrile, 16.0 g (0.079 mol) of 2,4-dinitrochlorobenzene and 5.5 g (0.095 mol) of finely divided dry potassium fluoride. After the air in the reaction vessel was displaced with nitrogen gas, the contents of the vessel were stirred at 235° C. (under 2.5 kg/cm$^2$·G) for 3 hours. After the reaction terminated, the resultant reaction mixture was cooled to room temperature and potassium chloride and unaltered potassium fluoride suspended in the reaction mixture were removed by filtration. When the benzonitrile solution remaining as the mother liquid was analyzed by gas chromatography using 1 m of a packing agent (SE 52) at a column temperature of 120° C., it was found to contain 94.0 mol % of 2,4-dinitrofluorobenzene based on the amount of 2,4-dinitrochlorobenzene first placed in the vessel.

EXAMPLE 16

An autoclave made of stainless steel and having an inner volume of 100 cc was charged with 40 g of benzonitrile, 8.0 g (0.028 mol) of hexachlorobenzene and 14.6 g (0.252 mol) of finely divided dry potassium fluoride. After the air in the reaction vessel was displaced with nitrogen gas, the contents of the vessel were stirred at 350° C. (under 16.0 kg/cm$^2$·G) for 30 hours. After the reaction terminated, the reaction mixture was cooled to room temperature and potassium chloride and unaltered potassium fluoride were removed by filtration. When the benzonitrile solution remaining as the mother liquid was analyzed by gas chromatography using 2 m of a packing agent (Thermon 1000) at a column temperature of 60° to 120° C. (gradual elevation), it was found to contain 20.3 mol % of hexafluorobenzene, 57.1 mol % of monochloropentafluorobenzene and 10.6 mol % of dichlorotetrafluorobenzene respectively based on hexachlorobenzene first placed in the vessel.

EXAMPLE 17

An autoclave made of stainless steel and having an inner volume of 100 cc was charged with 40 g of benzonitrile, 12.0 g (0.0811 mol) of 2,5-dichloropyridine and 12.3 g (0.212 mol) of finely divided dry potassium fluoride. After the air in the reaction vessel was displaced with nitrogen gas, the contents of the vessel were stirred at 370° C. (under 22.5 kg/cm$^2$·G) for 24 hours. By the use of a rotary evaporator, the reaction solution was freed from potassium chloride and unaltered potassium fluoride under a vacuum. When the benzonitrile solution remaining as the mother liquid was analyzed by gas chromatography using 2 m of a packing agent (Thermon 1000) at a column temperature of 60° C., it was found to contain 66.6 mol % of 2,5-difluoropyridine and 25.4 mol % of 5-chloro-2-fluoropyridine respectively based on the amount of 2,5-dichloropyridine first placed in the vessel. The peaks were confirmed by gas chromatographic mass spectrometry (GC-MS) to be those of 2,5-difluoropyridine and 5-chloro-2-fluoropyridine respectively.

What is claimed is:

1. A method for the manufacture of an organic fluorine compound represented by the general formula VIII:

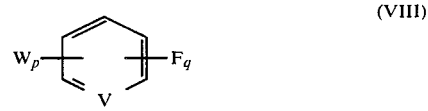

wherein V denotes N, CW, or CF where W is Cl, Br, CN or NO$_2$, p denotes an integer of the value of 0 to 4, and q denotes an integer of the value of 1 to 5, providing that the sum of p and q is an integer of the value of not more than 5, which comprises causing a chloro- or bromo-organic compound represented by the general forumla I:

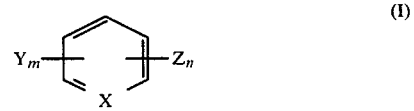

wherein X denotes N, —CY or —CZ where Y is Cl or Br and Z is F, CN or NO$_2$, m denotes an integer of the value of 1 to 5, and n an integer of the value of 0 to 4, providing that the sum of m and n is an integer of the value of not more than 5 to react with at least one fluorinating agent selected from the group consisting of alkali metal fluorides and alkaline earth metal fluorides in benzonitrile as a solvent at temperatures in the range of 190° to 400° C. under at least spontaneously generated pressure whereby at least one of said Y halogens is replaced by F.

2. A method according to claim 1 wherein said fluorinating agent is an alkali metal fluoride.

3. A method according to claim 1 wherein said chloro- or bromo-organic compound represented by the general formula I is used in an amount of about 5 to about 50 parts by weight based on 100 parts by weight of benzonitrile.

4. A method according to claim 1 wherein said fluorinating agent is used in an amount at least equivalent to the chlorine or bromine atom in said chloro- or bromo-organic compound represented by the general formula I to be substituted by a fluorine atom.

5. A method according to claim 1 wherein said alkali metal fluoride is used in an amount of 1 to 2 mols relative to the chlorine or bromine atom in said chloro- or bromo-organic compound represented by the general formula I to be substituted by a fluorine atom.

6. A method according to claim 2 wherein said alkali metal fluoride is potassium fluoride.

7. A method according to claim 1 wherein said compound represented by the general formula I is a compound represented by the general formula IV:

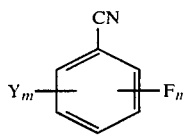

(IV)

wherein Y denotes Cl or Br, m denotes an integer of the value of 1 to 5, and n denotes an integer of the value of 0 to 4, providing that the sum of m and n is an integer of the value of not more than 5, and said compound represented by the general formula VIII is a compound represented by the general formula XI:

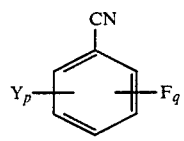

(XI)

wherein Y denotes Cl or Br, p denotes an integer of the value of 0 to 4, and q denotes an integer of the value of 1 to 5, providing that the sum of p and q is an integer of the value of not more than 5.

8. A method for the manufacture of pentafluorobenzonitrile according to claim 7 wherein said compound represented by the general formula XI is pentachlorobenzonitrile and the reaction is carried out at temperatures in the range of 270° to 400° C.

9. A method according to claim 1 wherein said compound represented by the general formula I is a compound represented by the general formula V:

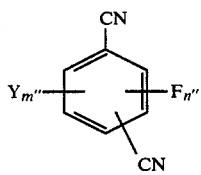

(V)

wherein Y denotes Cl or Br, m″ denotes an integer of the value of 1 to 4, and n″ denotes an integer of the value of 0 to 3, providing that the sum of m″ and n″ is an integer of the value of not more than 4, and said compound represented by the general formula VIII is a compound represented by the general formula XII:

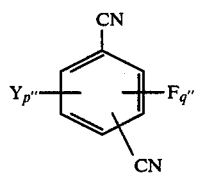

(XII)

wherein Y denotes Cl or Br, p″ denotes an integer of the value of 0 to 3, and q″ denotes an integer of the value of 1 to 4, providing that the sum of p″ and q″ is an integer of the value of not more than 4.

10. A method for the manufacture of tetrafluorophthalonitrile according to claim 9 wherein said compound represented by the general formula V is tetrachlorophthalonitrile and the reaction is carried out at temperatures in the range of 190° to 300° C.

11. A method for the manufacture of tetrafluoroisophthalonitrile according to claim 9 wherein said compound represented by the general formula V is tetrachloroisophthalonitrile and the reaction is carried out at temperatures in the range of 250° to 350° C.

12. A method for the manufacture of tetrafluoroterephthalonitrile according to claim 9 wherein said compound represented by the general formula V is tetrachloroterephthalonitrile and the reaction is carried out at temperatures in the range of 210° to 330° C.

13. A method according to claim 1 wherein said compound reperesented by the general formula I is a compound represented by the general formula VI:

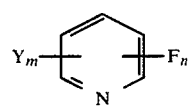

(VI)

wherein Y denotes Cl or Br, m denotes an integer of the value of 1 to 5, and n denotes an integer of the value of 0 to 4, providing that the sum of m and n is an integer of the value of not more than 5, and said compound represented by the general formula VIII is a compound represented by the general formula XIII:

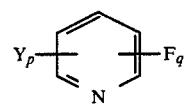

(XIII)

wherein Y, p and q are as defined claim 1.

14. A method for the manufacture of pentafluoropyridine according to claim 33 wherein said compound represented by the general formula VI is pentachloropyridine and the reaction is carried out at temperatures in the range of 300° to 400° C.

15. A method according to claim 1 wherein said compound represented by the general formula V is a compound represented by the general formula VII:

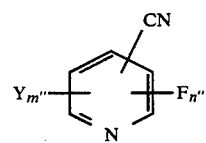

(VII)

wherein Y denotes Cl or Br, m″ denotes an integer of the value of 1 to 4, and n″ denotes an integer of the value of 0 to 3, providing that the sum of m″ and n″ is an integer of the value of not more than 4, and said compound represented by the general formula VIII is a compound represented by the general formula XIV:

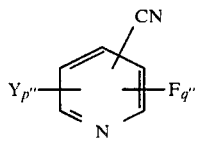 (XIV)
wherein p" denotes an integer of the value of 0 to 4, and q" denotes an integer of the value of 1 to 5.
16. A method according to claim 1 wherein said reaction is carried out in the presence of a phase transfer catalyst.
17. A method according to claim 16 wherein said phase transfer catalyst is used in an amount of 0.01 to 0.25 mol based on 1 mol of said chloro- or bromo-organic compound.
* * * * *